United States Patent [19]
Maciunas et al.

[11] Patent Number: 5,984,930
[45] Date of Patent: Nov. 16, 1999

[54] BIOPSY GUIDE

[75] Inventors: Robert Maciunas; J. Michael Fitzpatrick; Calvin R. Maurer, Jr., all of Nashville, Tenn.; Jennifer J. McCrory, Lincoln, R.I.; Rory Randall, San Diego, Calif.

[73] Assignee: George S. Allen, Nashville, Tenn.

[21] Appl. No.: 08/723,402

[22] Filed: Sep. 30, 1996

[51] Int. Cl.$^6$ ................................................. A61B 19/00
[52] U.S. Cl. ............................ 606/130; 600/417; 600/429
[58] Field of Search .................................. 600/417, 429; 606/1, 130, 108

[56] References Cited

U.S. PATENT DOCUMENTS

| | | | |
|---|---|---|---|
| 2,697,433 | 12/1954 | Zehnder | 606/130 |
| 3,115,140 | 12/1963 | Volkman . | |
| 3,457,922 | 7/1969 | Ray . | |
| 4,386,602 | 6/1983 | Sheldon et al. . | |
| 4,465,069 | 8/1984 | Barbier et al. . | |
| 4,592,352 | 6/1986 | Patil . | |
| 4,602,622 | 7/1986 | Bar et al. . | |
| 4,617,925 | 10/1986 | Laitinen . | |
| 4,638,798 | 1/1987 | Shelden et al. . | |
| 5,030,223 | 7/1991 | Anderson et al. | 606/130 |
| 5,257,998 | 11/1993 | Ota et al. | 606/130 |
| 5,280,427 | 1/1994 | Magnusson et al. . | |
| 5,320,628 | 6/1994 | Ufkin | 606/130 |
| 5,387,220 | 2/1995 | Pisharodi | 606/130 |
| 5,695,501 | 12/1997 | Carol et al. | 606/130 |

FOREIGN PATENT DOCUMENTS

WO 95/22297  8/1995  WIPO .

Primary Examiner—Glenn K. Dawson
Attorney, Agent, or Firm—Kenyon & Kenyon

[57] ABSTRACT

A surgeon can select an entry point and a target point in a preoperative image volume of the patient. The target point and entry point form a trajectory line along which the surgeon wishes to perform a surgical procedure such as a biopsy and line up a surgical instrument. Once a surgical platform is moved along a guide arm arc close to a point on the trajectory line, the surgical platform is locked to the guiding arm. A pivot point position at the center of a ball joint in the middle of a metal plate is then arranged to be exactly at a point on the trajectory line. The metal plate is locked down and the ball joint is rotated to ensure that the surgical sleeve extends exactly along the trajectory line. This allows a decoupling between the position and orientation movements required to line the surgical sleeve up with the trajectory line to perform a surgical procedure. An interoperative localization device (ILD) is used to track the position of the surgical guide relative to the image space.

25 Claims, 16 Drawing Sheets ial system at the center of 50 the ring.

BIOPSY GUIDE

BACKGROUND OF THE INVENTION

The present invention relates to a biopsy guide in which surgical devices can be accurately positioned relative to an image.

A variety of devices have previously been used during surgery to position a patient in an operating room and so that the position of a particular location on a patient can be accurately located.

U.S. Pat. No. 4,617,925 to Laitinen discloses an adaptor for definition of the position of brain structures. This is implemented using spatial coordinates in computerized tomography and NMR examination and transferring the coordinates to a stereotactic apparatus. The adaptor includes supports for holding a patient's head in place.

U.S. Pat. No. 4,386,602 to Sheldon et al. relates to an intracranial surgical operative apparatus. The apparatus in this patent is used for operating on the brain with minimal disturbances.

U.S. Pat. No. 4,465,069 to Barbier et al. relates to the cranial insertion of a surgical needle utilizing computer-assisted tomography.

U.S. Pat. No. 5,257,998 to Ota et al. relates to a medical three-dimensional locating apparatus capable of accurately reproducing the three-dimensional position data of a focus obtained through an imaging diagnosis in an affected part of a patient body for an actual surgical operation. This patent additionally discusses the selection of an optimum approach angle of a direction to approach the focus point along a reference line through a simple operation.

U.S. Pat. No. 4,592,352 to Patil discloses a computer-assisted tomography stereotactic system. The system disclosed in the Patil patent discloses an apparatus for performing surgical procedures through a patient's skull to a target within the skull using a computer-assisted tomography scanner.

U.S. Pat. No. 4,602,622 to Bär et al. discloses a computer tomography apparatus producing transverse layer images. A patient-targeting device is used to introduce a biopsy needle into a patient along a path determined by the targeting device.

U.S. Pat. No. 4,638,789 to Shelden et al. discloses a stereotactic method and apparatus for locating and treating or removing lesions. The apparatus defines points in a region using a three-dimensional coordinate system with reference to a ring attached to the patient to establish a reference point for the three-dimensional coordinate system at the center of the ring.

U.S. Pat. No. 5,387,220 to Pisharodi discloses a stereotactic frame and localization method incorporating localization frames which is operable without the use of head pins or screws. Several natural cranial reference points are initially established. Once the natural reference points are established, localization is performed using a spherical coordinate system incorporating lines, planes and angles referenced on and within the head.

U.S. Pat. No. 5,280,427 to Magnusson et al. discloses a puncture guide for computer tomography. A needle of a tissue sampling device is guided to a target location within the body of a patient. The biopsy needle is directed along a desired path and the depth of penetration of the needle is controlled to prevent accidental overpenetration of the needle. The guidance device is not limited to the plane perpendicular to a longitudinal axis of the patient but is also capable of guiding the needle in a plane which is neither perpendicular or parallel to the longitudinal axis.

Previous guiding devices are difficult in providing an image guided surgical system which may be used during surgery without complicated coordinate system calculations.

SUMMARY OF THE INVENTION

The present invention relates to a surgical guiding arrangement in which a surgical instrument may be positioned accurately relative to a target point and an entry point of the patient and along a trajectory line through the entry point and target point of the patient.

A surgical platform is first moved along a guiding arm arc close to a point along the trajectory extending through the entry point and the target point of the patient. This position on the trajectory line is any point external to the patient's head. Prior to sliding of the surgical platform along the guiding arm, the patient's head is fixed rigidly to a head clamp which is fixed to an operating table. The guiding arm arc swivels, for example, about two joints at one end of the guiding arm. Once the guiding arm arc is moved into a position so that a portion of the guiding arm arc is near the entry point and/or trajectory line, the guiding arm arc is locked in position. Then the surgical platform is moved along the guiding arm arc until the surgical platform is near the trajectory line. The surgical platform is then locked to the guiding arm arc. A metal plate within the surgical platform is then moved in two dimensions until a ball joint pivot point at the middle of the metal plate is at a point along the trajectory line. The metal plate is then locked in place. The ball joint is then rotated so that the surgical sleeve extends exactly along the trajectory line. In this manner, the two dimensional translation of the surgical platform is completely separated from the two dimensional rotation of the ball joint. The surgical sleeve is moved into position along the trajectory line extending between the entry point and the target point on the patient's head without any complicated calculations being required.

The navigational software allows the surgeon to accurately move the pivot point to a point along the trajectory line while looking at an image comparing the position of the pivot point with a position on the trajectory line. Then, the navigational software allows the surgeon to view on the image the difference between the angle of the surgical sleeve relative to the trajectory line until the surgical sleeve is lined up exactly along the trajectory line.

DETAILED DESCRIPTION

Figure 1:
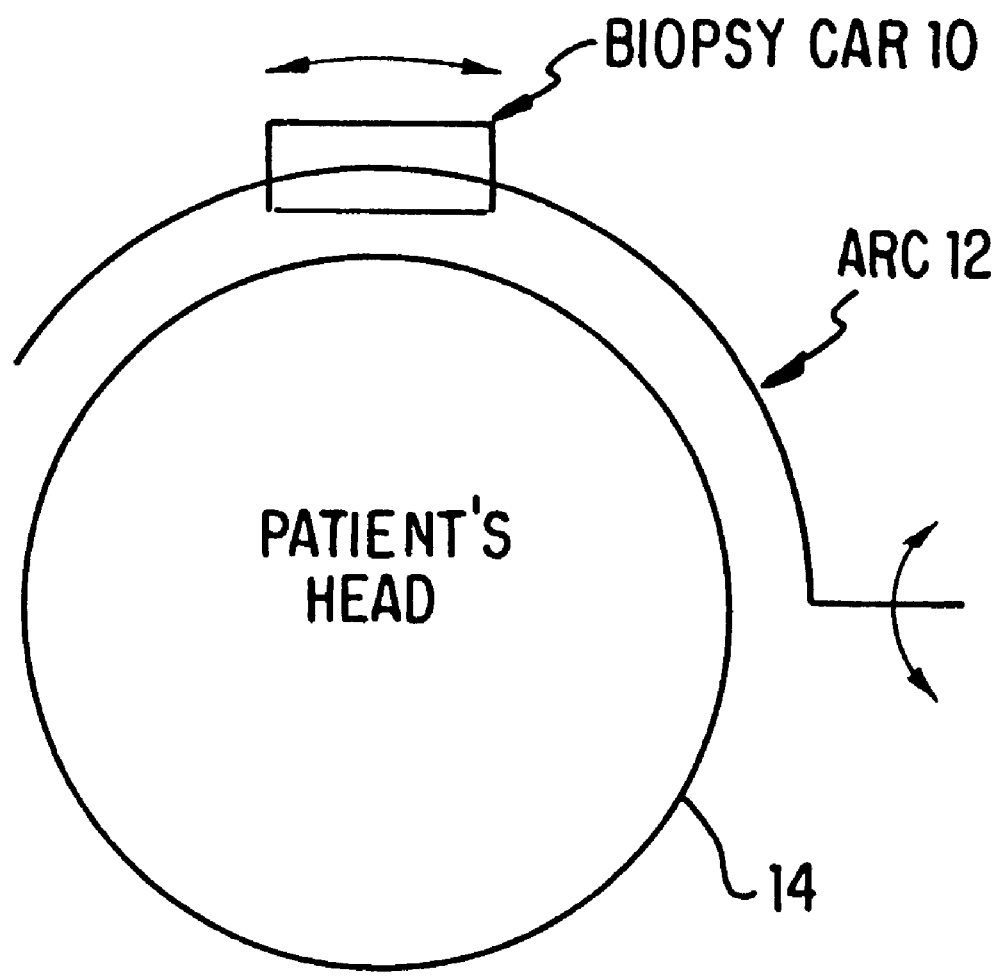
FIG. 1 illustrates an arrangement according to an embodiment of the present invention.

In a surgical device system (or biopsy device system) according to an embodiment of the present invention, a neurosurgeon selects an "entry" point and a "target" point in a preoperative image volume (e.g., CT or MR). The target point is the point the neurosurgeon wishes to reach, e.g., to obtain a sample of tissue or implant an electrode. The entry point is the point on the skull that the neurosurgeon wishes to go through to reach the target point. The entry point and the target point together define a "trajectory," (i.e., the line passing through these two points). The general purpose of the surgical device (biopsy device) is to direct a surgical needle (such as a biopsy needle or electrode or whatever) such that it passes through the entry point and stops at the target. Biopsy devices are an integral part of most stereotactic frame systems. The biopsy device according to the present invention may be used for any frameless image-guided surgical navigation systems.

The first step in the surgical guide system (biopsy guide system) according to an embodiment of the present invention, is getting a surgical platform (biopsy car or biopsy platform) close to the trajectory. One embodiment uses a guide arm arc and a biopsy car that slides along the guide arm arc. The patient's head is rigidly fixed in a head clamp such as a Mayfield® head clamp. The head clamp is affixed to an operating table. The arc is rigidly attached to the head clamp. Alternatively, the arc could instead be attached to the operating table or to something else rigidly attached to the table. In one embodiment, the arc swivels about its two joints at one end. Alternatively, the arc could swivel about its two ends. The biopsy platform is connected to the biopsy car that slides along the arc. With these various degrees of freedom, the biopsy platform can be placed over a wide region of the head.

It is noted that frame-based surgical devices (biopsy devices) typically work with a specific geometrical design (e.g., a circular arc with a specific radius). The image coordinates of the entry and target points are converted to physical space coordinates, and these are converted to a set of biopsy device parameters (e.g., arc angles and position along the arc). Thus, frames-based biopsy devices require the arc to be carefully constructed and calibrated. In the present invention, the arc serves as a device to get the biopsy platform close to the trajectory, and thus does not need to be as carefully constructed. The primary requirement of the arc is that it be mechanically sturdy. In fact the present invention could be implemented without an arc, although it may be the easiest way to manufacture a mechanically solid support. Another approach according to an embodiment of the present invention, is to have the biopsy platform connected to a multi-jointed arm that is in turn rigidly attached to the head clamp or the operating table.

In one embodiment of the present invention, the biopsy platform consists of a movable metal plate sandwiched within an annular metal support. The metal plate can be locked in place with a set screw, for example. A ball joint is located in the center of the metal plate. A biopsy sleeve passes through the middle of the ball joint and can accommodate both an intraoperative localization device (ILD) and a biopsy guide. The ball joint can be locked in place with a set screw. In one embodiment of the present invention, the biopsy platform is connected to the biopsy car with a screw. The biopsy platform can be moved by loosening the screw.

After getting the biopsy platform close to the trajectory, the position of a pivot point and orientation of the biopsy sleeve is set as follows. The pivot point is located at the center of the ball joint. First, the present inventors have recognized that it is not necessary to be at the entry point (e.g., of the body) but rather need only be on the trajectory. Second, it is recognized that position and orientation may be decoupled. Because it is necessary to be on the trajectory rather than at a specific point on the line, the biopsy sleeve can be positioned with a two-dimensional (2D) translation of the biopsy platform. The biopsy platform does not need to be perpendicular to the trajectory. The ILD is placed in the biopsy sleeve. In an embodiment of the present invention, the ILD is a probe connected to a handle with infrared emitting diodes (IREDs) that are tracked by an optical position sensor (OPS), but which could also be for other frameless systems different types of devices, e.g., an articulated mechanical arm, an electromagnetic device, or an ultrasonic device. The biopsy platform (or metal plate) is moved until the ILD position, which is calibrated such that it corresponds to the center of the ball joint (or pivot point), is on the trajectory. When it is on the trajectory, the metal plate is locked in place.

The proper two-dimensional transitional movement can be accomplished as follows. An image volume consisting of slices perpendicular to the trajectory is created. The navigation system converts the physical space position of the ILD to the image coordinate system. The position of the ILD relative to the image is displayed on the screen along with the position of the trajectory in the appropriate image slice. The plate is moved until the position of the ILD coincides with the position of the trajectory. Additional information can be provided to make the task easier, e.g., a zoomed image and/or the distance of the ILD from the trajectory.

According to one embodiment of the present invention, only gross manual adjustment of the surgical platform is necessary. Finer control of movement might be accomplished using screws. In fact, screws for both coarse and fine position adjustment may be used.

After the ILD position (e.g., the position of the pivot point) is translated such that it is on the trajectory (and thus the center of the ball joint is on the trajectory), the ball joint is rotated until the orientation of the ILD (and thus the orientation of the axis of the biopsy sleeve) coincides with the orientation of the trajectory. When the proper orientation is found, the ball joint is locked in place. The proper orientation can be achieved as follows. An image volume consisting of slices perpendicular to the trajectory is created. The navigation system converts the position and orientation of the ILD in physical space to the position and orientation in the image coordinate system. This information is used to calculate the intersection of the trajectory of the ILD (and thus the trajectory of the axis of the biopsy sleeve) with the image slice that passes through the target and is perpendicular to the desired entry-target trajectory. The position of both this intersection and the target is displayed in this slice. The ball joint is rotated until this intersection coincides with the target. Again, additional information can be provided to make the task easier, e.g., a zoomed image and/or the distance of the intersection from the target. Additionally, in one embodiment of the present invention, the slice passing through the target is displayed. However, any image slice could be displayed according to other embodiments of the present invention.

After the proper translation of the biopsy platform (metal plate) and rotation of the ball joint is achieved, the distance between the ILD position (i.e., the position of the center of the ball joint or pivot point) and the target is calculated by the navigation system software. Although it is not important to be at a specific point on the trajectory, it is important to know the location on the trajectory of the pivot point (i.e., the center of the ball joint). At this point, a variety of tasks can be performed. A biopsy can be accomplished by placing a biopsy guide into the sleeve and then using traditional biopsy techniques. The use of the distance between the pivot point and the target to set a collar or stop on a biopsy needle is straightforward. It is also possible to perform an image-guided biopsy. IRED's could be placed on the biopsy needle and tracked by the optical position sensor (OPS). This implementation is also extendable to other frameless systems. For example, an ultrasonic navigation system could be used to accomplish an image-guided biopsy by placing spark gaps on the biopsy needle.

Many neurosurgery procedures require a precise location of a stable platform holding the tools used in those procedures. Previous methods of implementing the stable platform for holding the tools used in such surgical procedures involved frames which are physically attached to the patient's head. The ability to attach, detach and re-attach the surgical platform and/or surgical guide while maintaining a sterile field around the patient has become very important.

The present invention provides a surgical guide including a surgical platform that will remain stable under normal surgical conditions and a guide arm allowing the surgeon to precisely locate the platform using computer guided feedback. The system is not directly connected to the patient and is capable of attachment and detachment with no impact on the integrity of the sterile field.

A surgical guide according an embodiment of the present invention includes an attachment bar, a guide arm (or arc) and a surgical platform. In biopsy procedures, a biopsy needle guide is used to provide stability while tracking the biopsy needle.

An attachment bar is connected to a starburst joint at a base of a Mayfield®-type skull clamp (or other type head clamp). The guide arm (or arc) is connected to one side of the attachment bar. The guide arm provides support for the surgical platform. The guide arm allows the surgical platform (or biopsy car) to be positioned on a theoretical sphere around the patient's head and can be adjusted in at least two ways. The guide arm can be moved closer to or further from the head by sliding it along a shaft extension on the attachment arm. The guide arm can also be rotated around a theoretical center of the head in a manner similar to the rotation of the visor of a helmet. The guide arm is locked by a knob for sliding and a lever for rotating independently.

The guide arm sliding and rotating motion can be used to adjust and locate the correct position of the surgical platform relative to a predetermined entry point and target point of a patient. The surgical platform (or biopsy car) can slide and lock along the entire length of the guide arm arc to provide an additional gross adjustment. The guide arm sliding and rotating adjustment and the platform sliding and locking adjustment along the guide arm arc provide three gross (course) adjustments to provide access to most regions of surgical interest near a patient (for example, regions of interest on a patient's head).

A surgical platform (or biopsy car) is a surgical platform where the tools required for the surgical procedure are located. For example, a biopsy needle may be provided at the surgical platform. A surgeon uses the guide arm arc as a track and, for example, using rollers to slide along the guide arm arc, can be locked in a general position to provide a position for a pivot point ball joint near the entry site of the patient. The surgical tools are held in the pivot ball joint which can also be adjusted for a particular desired angular approach to the target site. The surgical platform includes two fine adjustment or location parameters. As a first fine adjustment for the guide arm, two sliding surfaces with a locking lever allow the center of the pivot ball joint to be precisely positioned on the previously determined approach vector (or trajectory). A second adjustment contained in the pivot ball joint assembly allows the surgical tools to be precisely oriented to the correct approach angle. Fine adjustment of the surgical approach is contained in the pivot ball joint assembly in Phi, theta and the angle relative to the tangent of the theoretical sphere.

A needle guide is required for a biopsy application according to an embodiment of the present application to maintain the planned trajectory for the entire length of the biopsy needle. The needle guide allows the surgeon to define the point of the biopsy needle to be tracked with application software (for example, Acustar™ surgical navigation system software). The end tip of the biopsy needle may be choosen as the working point or the "working" portion of the needle may be tracked. It is important for some position along the biopsy needle guide to be tracked to determine the location thereof. A particularly advantageous location of the biopsy needle guide to be tracked is the point at which the surgical tool projects through the pivot ball joint. The ability to define the point to be tracked minimizes errors that can occur.

A surgeon can then verify the surgical approach trajectory in a visual manner using a localization guidance system and computer processed image software. The localization device is attached to the surgical tool in a well defined manner. The localization device used in an embodiment of the present invention can be an array of infrared emitting diodes read by a calibrated sensor.

The present invention provides a sterile surgery field integrity which can be easily maintained when attaching, detaching, and reattaching the guide arm and surgical platform for different procedures during one operating setup. Additionally, the present invention allows easy adjustment of a guidance system to accommodate different head sizes. Further, the present invention allows a stable and accurate positioning of the surgical platform by using a localization guidance system which eliminates the need to affix the platform to the patient's skull. According to the present invention, the platform position is adjustable in r, theta and phi directions. The pivot ball joint can be adjusted in x, y directions and the needle (surgical tool) can be rotated through a 90 degree cone. This allows a full coverage of the skull for most surgical procedures. The present invention additionally allows surgeon definition of the biopsy needle (or other tool) position to be tracked. Additionally, in conjunction with an image guided surgical system (for example, Acustar™ navigation software) the defined needle (or other surgical tool) position can be tracked in real time. The system additionally requires no calculations to be implemented in the operating room theater when used in conjunction with an image guided surgical system.

FIG. 1 illustrates an embodiment of the present invention. A biopsy car 10 (or surgical platform) slides back and forth along a guide arm (or arc) 12. Additionally, the arc 12 can rotate at least at one end thereof to cover large portions of the patient's head 14. The guide arm arc is attached to an attachment bar (not illustrated in FIG. 1) which can be attached to a head clamp such as a Mayfield®-type head clamp attached to the patient's head 14. The guide arm arc 12 is rotatable (swivel) at one or both ends thereof so that the guide arm arc 12 passes generally over a particular area of interest of the patient's head 14. The surgical platform 10 is slid along the guide arm arc 12 to a particular area of interest of the patient's head 14. The surgical platform 10 is then locked down on the arc 12.

Figure 3:
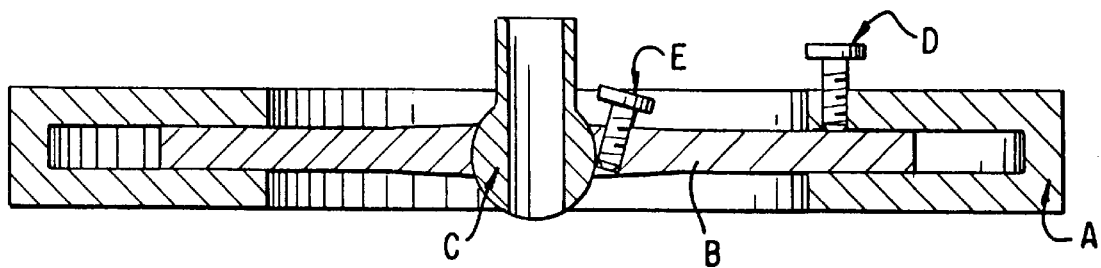
FIGS. 2 and 3 illustrates arrangements within a surgical platform according to an embodiment of the present invention.
Figure 2:
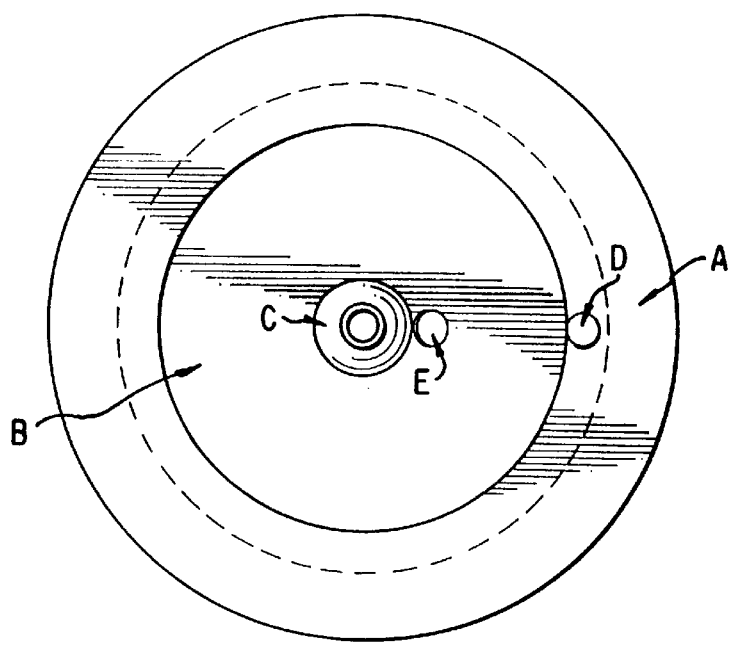

FIGS. 2 and 3 illustrate portions of the surgical platform 10 according to an embodiment of the present invention. FIG. 2 illustrates portions of the surgical platform from a top view and FIG. 3 illustrates sections of the surgical platform from a side view. Reference numeral A represents an annular metal support, reference numeral B represents a movable metal plate, reference numeral C represents a ball joint (or a pivot point) and reference numerals D and E represent set screws. Once the surgical platform (or biopsy car) 10 is locked down on the guide arm arc 12, the movable plate B is adjusted within the annular metal support A relative to a target point on the patient's head 14 until the middle of the ball joint C is on a point of a predefined trajectory line. Set screw D is then used to lock the movable metal plate B relative to the annular metal support A. Ball joint C can then be rotated to adjust and access of a surgical device sleeve along a particular trajectory line. Once the ball joint (pivot point C) has been adjusted in this matter, set screw E is used to lock ball joint C in position.

Figure 4:
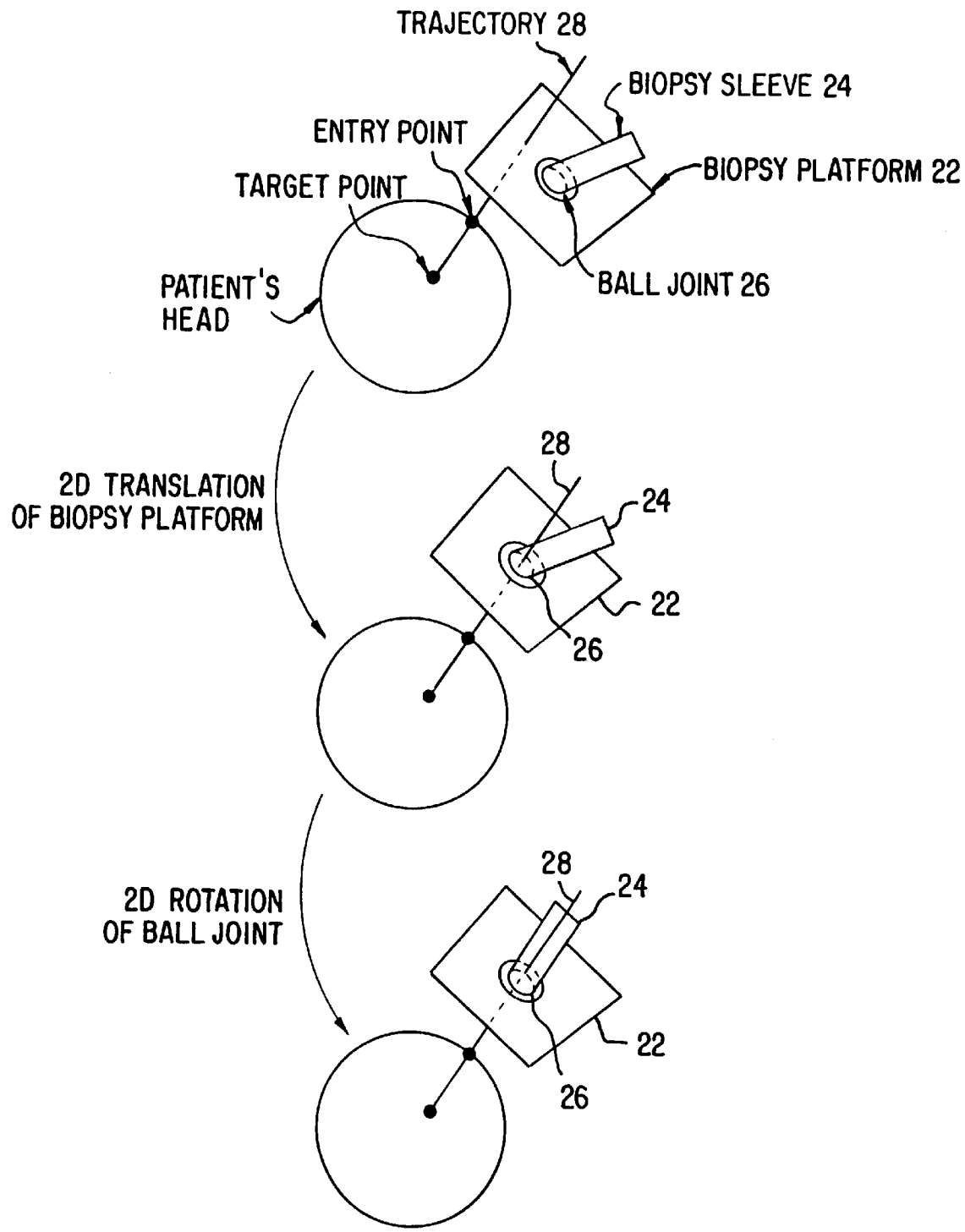
FIG. 4 illustrates separate translational and rotational movements according to an embodiment of the present invention.

FIG. 4 illustrates a method of adjusting the biopsy platform 22 and a biopsy sleeve 24 which extends through a ball joint 26 within the biopsy platform 22 relative to a trajectory 28. Trajectory 28 is a trajectory line in a pre-operative image, for example, which extends through an entry point and a target point of the patient's head. The biopsy platform 22 along with the biopsy sleeve 24 and ball joint 26 are translated in a two dimensional manner so that the ball joint 26 extends through any point along the trajectory line 28. The point along the trajectory is a point which is outside the patient's head but is somewhere along trajectory line 28. Once the center of the ball joint 26 has been moved to the trajectory line 28, the biopsy platform (for example, the metal plate B of FIGS. 2 and 3) is locked into position. Once the original two dimensional translation of the biopsy platform is performed to extend the center of the ball joint 26 to a point on a trajectory line 28, an additional rotation of the ball joint 26 is made to extend an access of the biopsy sleeve 24 to follow the trajectory line 28.

As illustrated in FIG. 4, the present invention allows a decoupling of different adjustments in order to line the surgical sleeve up with a trajectory line along a target and entry point of a patient. The present invention recognizes that a surgeon does not have to line up the swivel point at an entry point on the patient. The surgeon only needs to find the trajectory line and then rotate the surgical sleeve until the sleeve is lined up with a trajectory line on an image in the operating room. In order to provide feedback to the image data so that the surgeon can see if the surgical sleeve is lined up with the trajectory line within the image, the surgical sleeve can be provided with light emitting diodes (LEDs) to track the position in the operating room using, for example, the Acustar™ navigational software. The universal ball joint provided within the metal plate is used as a reference point. Once the biopsy sleeve has been oriented in the position of the trajectory line, the biopsy sleeve may be locked down and attaching and detaching of surgical instruments may be provided through the ball joint while the ball joint pivot point remains in a set position. Since the system navigation software knows the location of the target and the entry point on the patient's head and the reference point position of the ball joint, the distance from the ball joint (or metal plate) to the target can be calculated. Thus, when a biopsy probe or other surgical instrument is extended through the ball joint, the surgical instrument can be calibrated so that the surgeon can extend the surgical instrument through the ball joint directly to the target so that the tip of the surgical instrument is directly at the target without going past the target.

The present invention allows a surgeon to sit down with pre-operative images, for example, and pre-plan a target point, entry point, and a trajectory to be implemented in the surgery. The present invention then allows the surgeon to find the target and entry points and the trajectory along the target point and entry point at the time of surgery without performing any measurements from the images or any other sort of calculations.

The present invention additionally allows parallel trajectories to be used during a surgery. This can be implemented by finding a particular trajectory as defined above. Then the surgical platform (or biopsy car) can be unlocked and slid and locked on at a new point to provide a perfectly parallel trajectory line without any measuring or other sort of calculation.

Additionally, while the present invention has been described with respect to biopsy, the present invention can be implemented using any sort of other surgical instrument, including the passing of catheters or other functional neurosurgery (for example, guiding endoscope).

Figure 5:
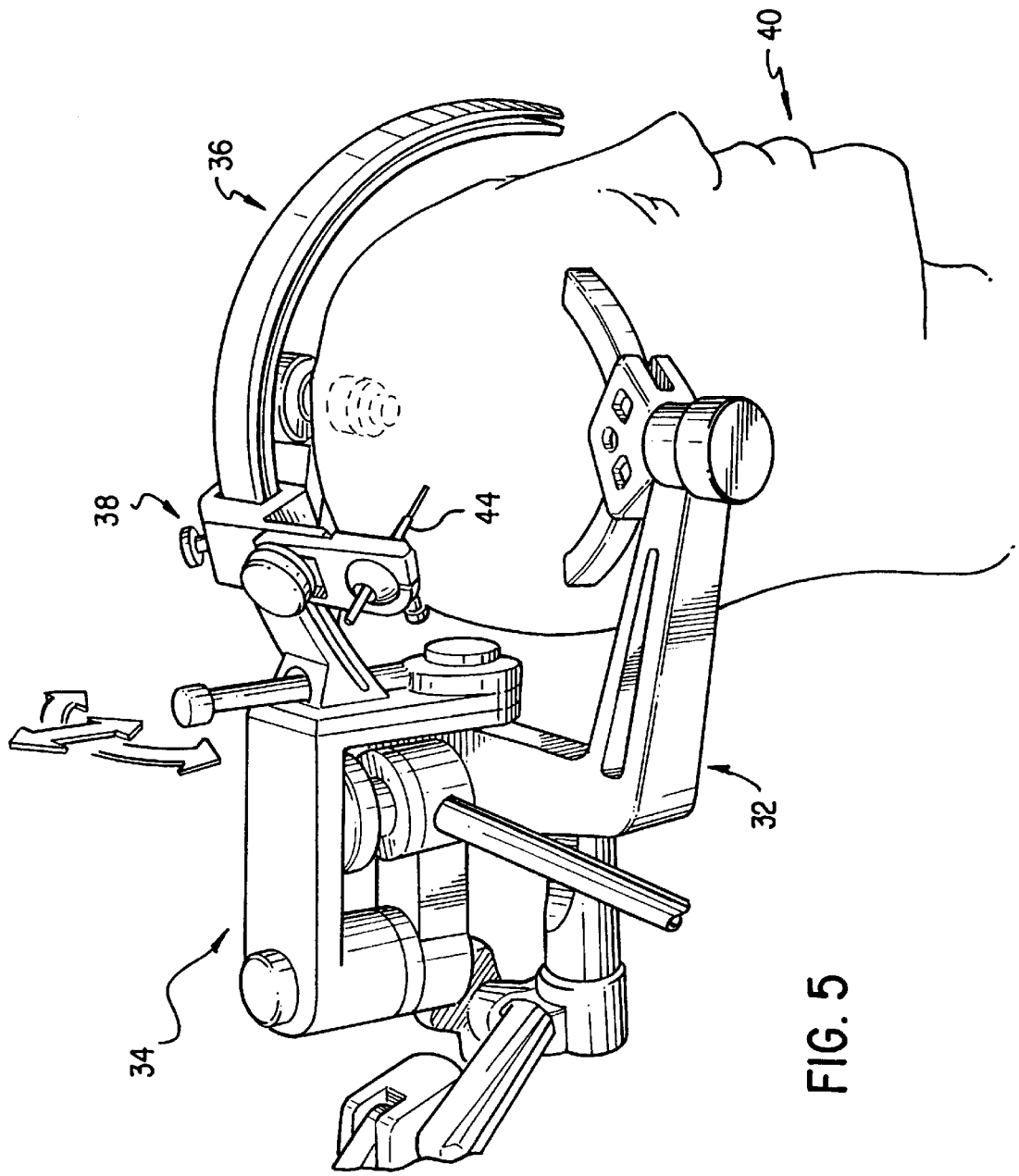
FIG. 5 illustrates an arrangement according to an embodiment of the present invention.
Figure 6:
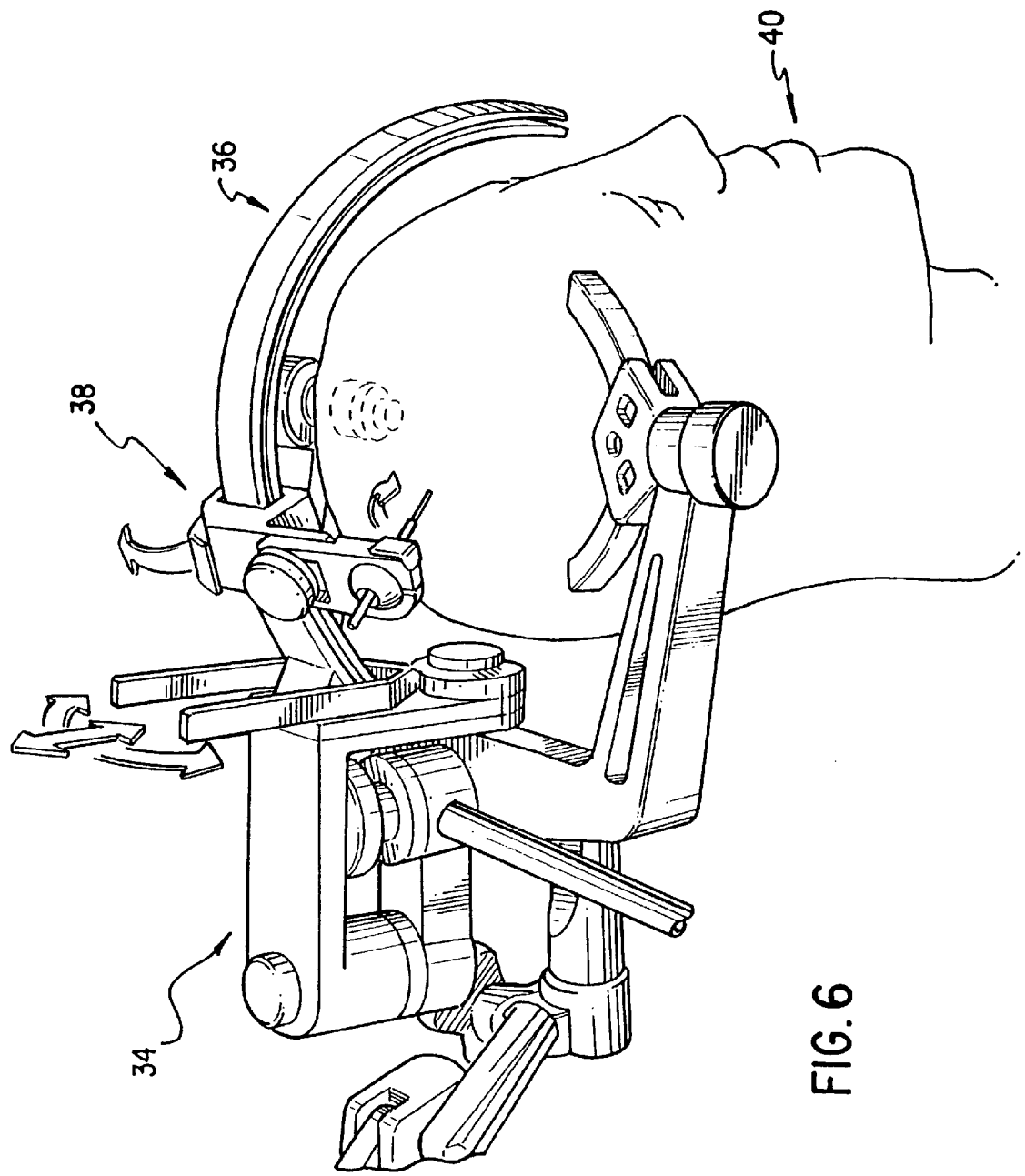
FIG. 6 illustrates an arrangement according to an embodiment of the present invention.

FIG. 5 illustrates an embodiment of the present invention including a head clamp 32, an attachment arm 34, a guide arm arc 36 and a surgical platform 38 all arranged around the patient's head 40. As illustrated in FIG. 5, the head clamp 32 is used to position the patient's head 40 relative to the surgical operation. For example, the head clamp 32 may be attached to an operating table. Guiding arm 36 can be adjusted relative to attachment 34 in an up and down or curved manner as illustrated by the arrows in FIG. 5. Additionally, surgical platform 38 slides along guiding arm arc 36 and holds a surgical instrument or surgical sleeve 44. FIG. 6 illustrates an arrangement similar to FIG. 5 and additionally shows another method of attachment between attachment arm 34 and guiding arm arc 36, and additional possible movement of surgical platform 38.

Figure 7:
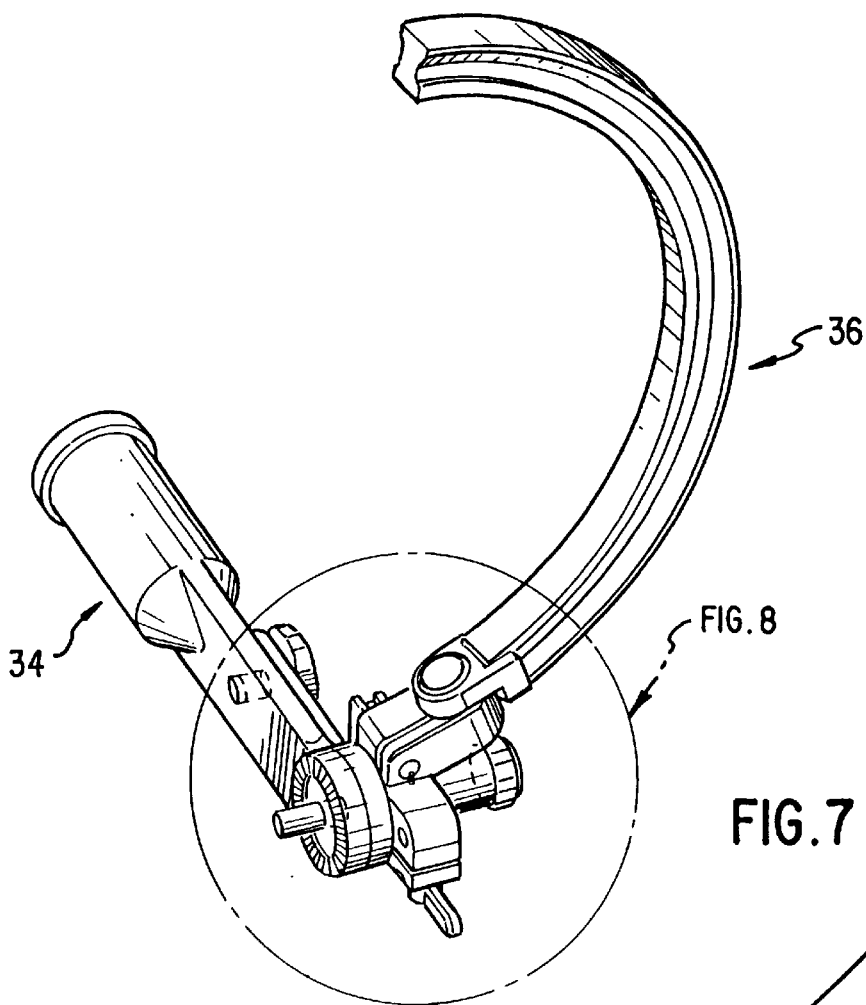
FIGS. 7, 8, 9, 10 and 11 illustrate relative arrangements between an attachment arm and a guiding arm according to embodiments of the present invention.
Figure 8:
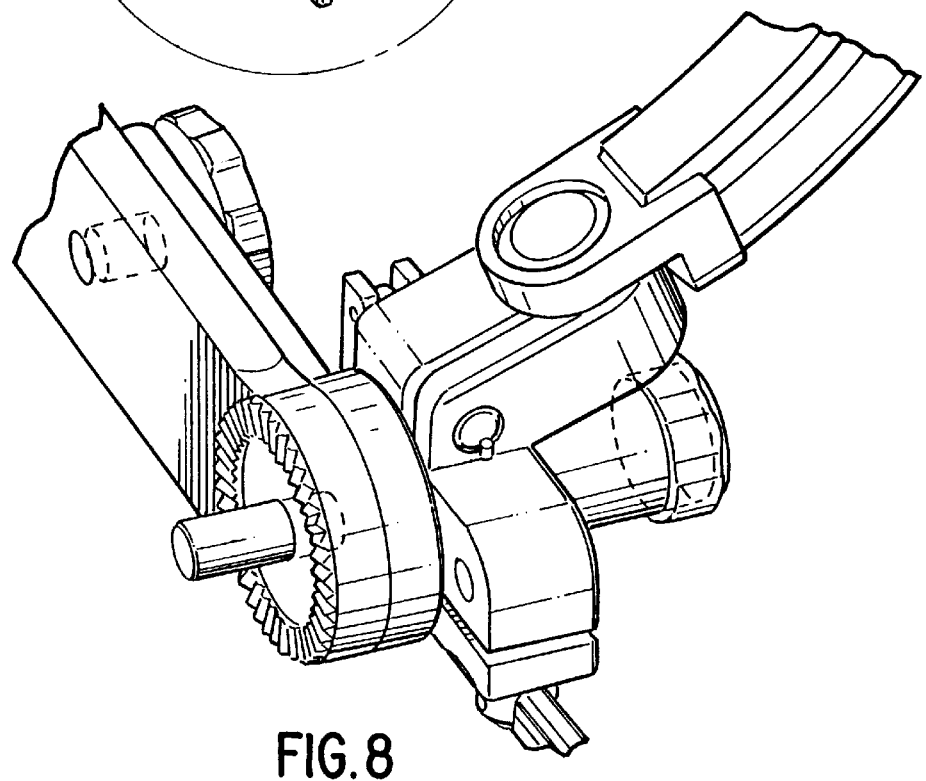

FIG. 7 illustrates a connection of an attachment arm 34 with a guided arm 36 according to an embodiment of the present invention. Further detail of the portion of FIG. 7 within the dotted circle line of FIG. 7 is illustrated in FIG. 8.

Figure 9:
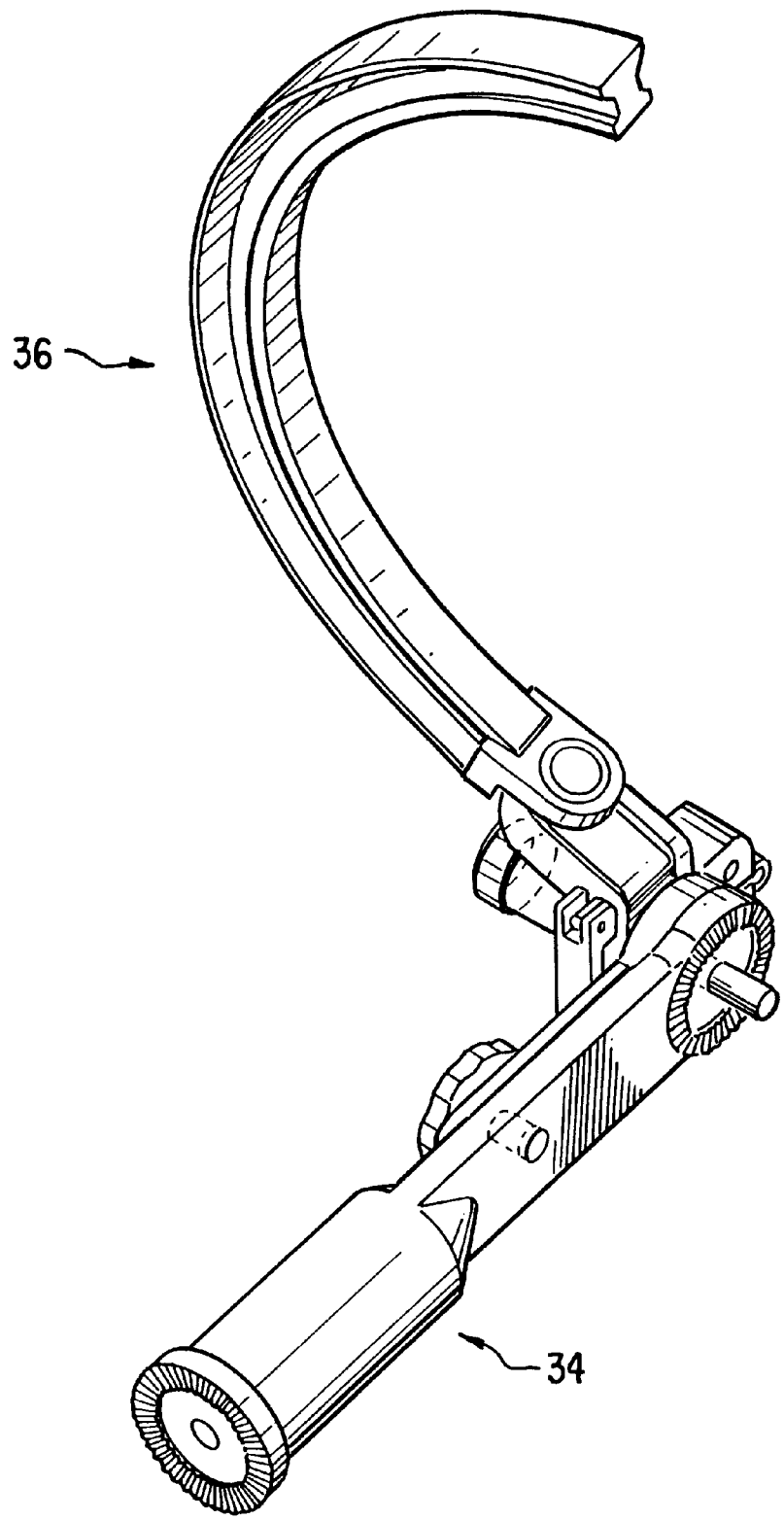
Figure 10:
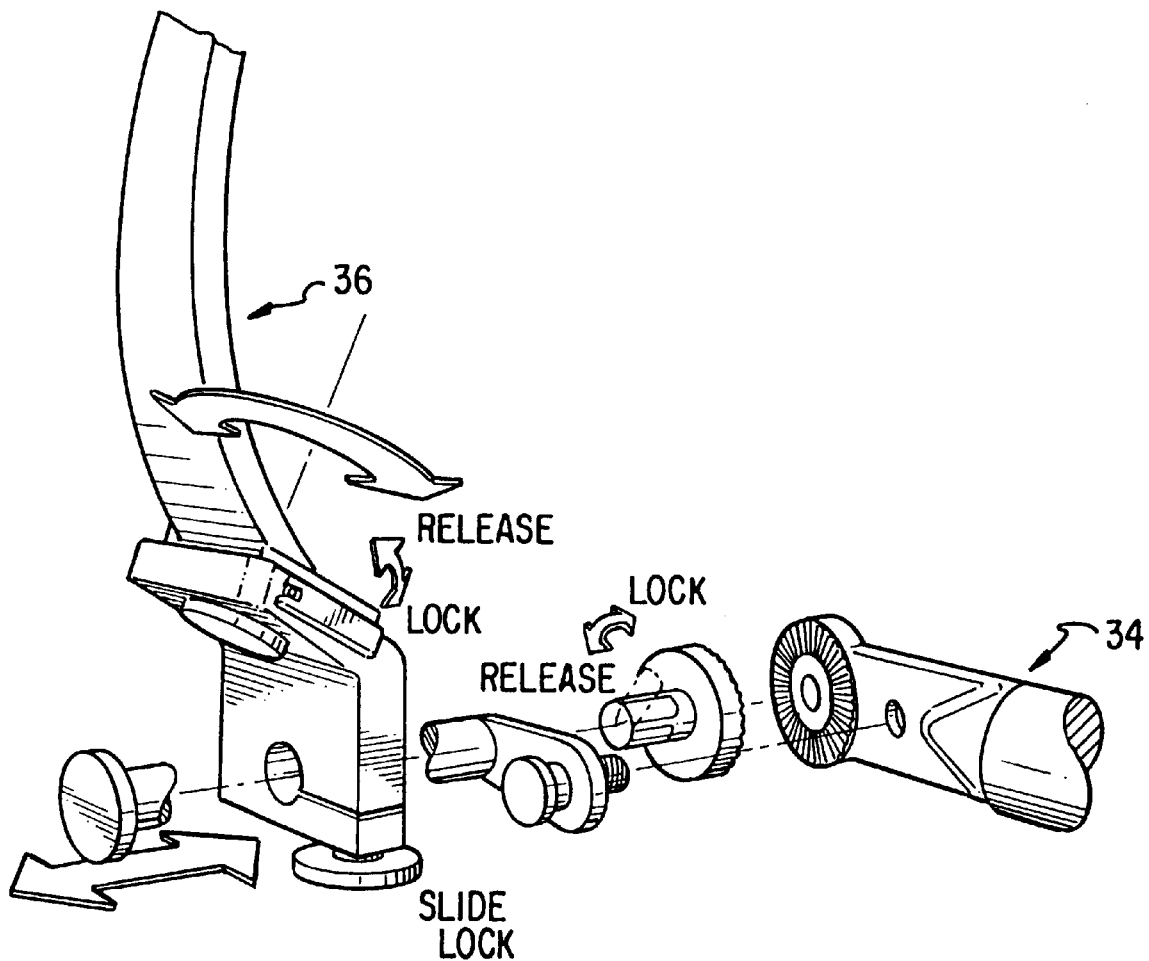

FIG. 9 shows an additional embodiment of the present invention of an attachment between attachment bar 34 and guiding arm 36 from a different angle. FIG. 10 illustrates a further combination between attachment bar 34 and guiding arm arc 36 according to an embodiment of the present invention. FIG. 10 illustrates further possible movement between attachment arm 34 and guiding arm 35 for original gross (course) movement of guiding arm 36 relative to the patient's head.

Figure 11:
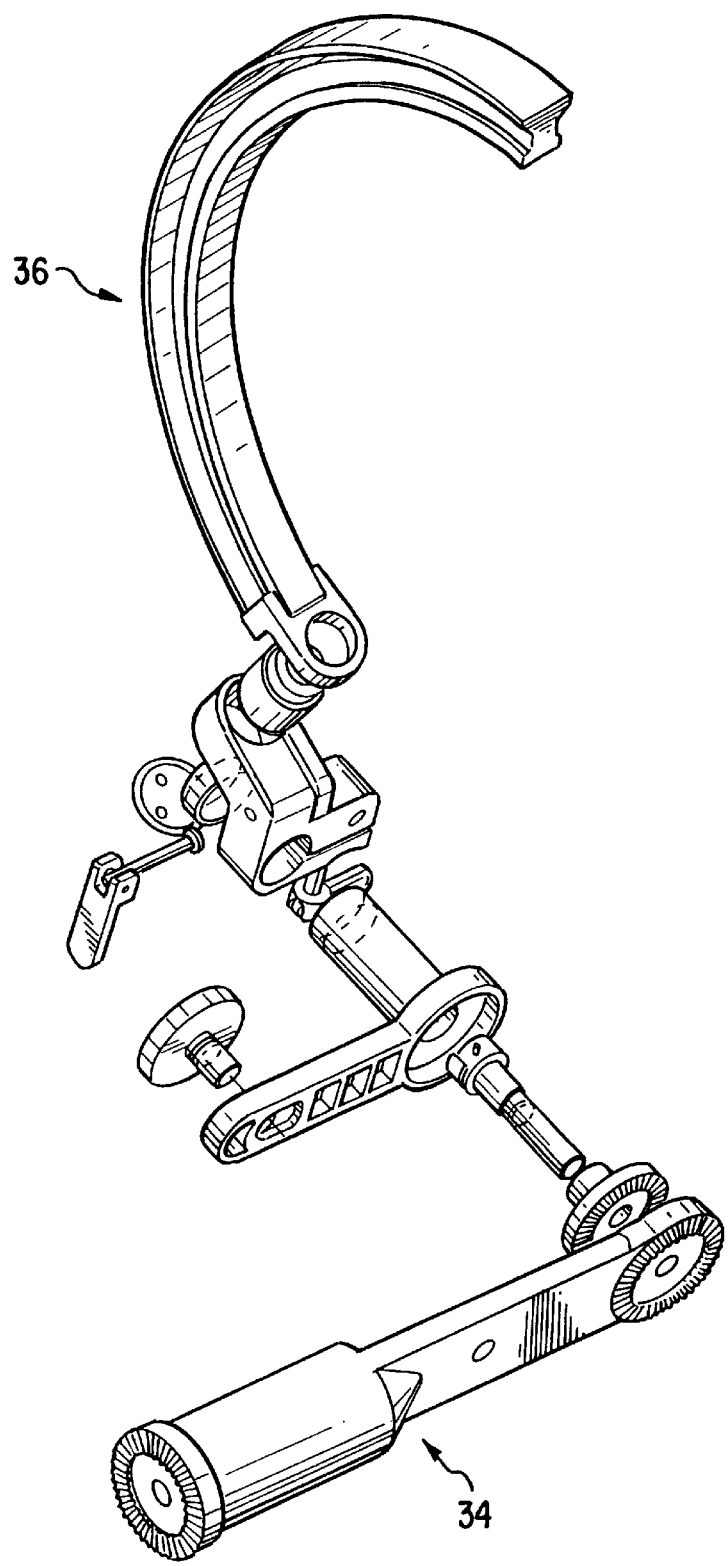

FIG. 11 illustrates further details of a connection between the attachment arm 34 and guiding arm 36 according to an embodiment of the present invention.

Figure 12:
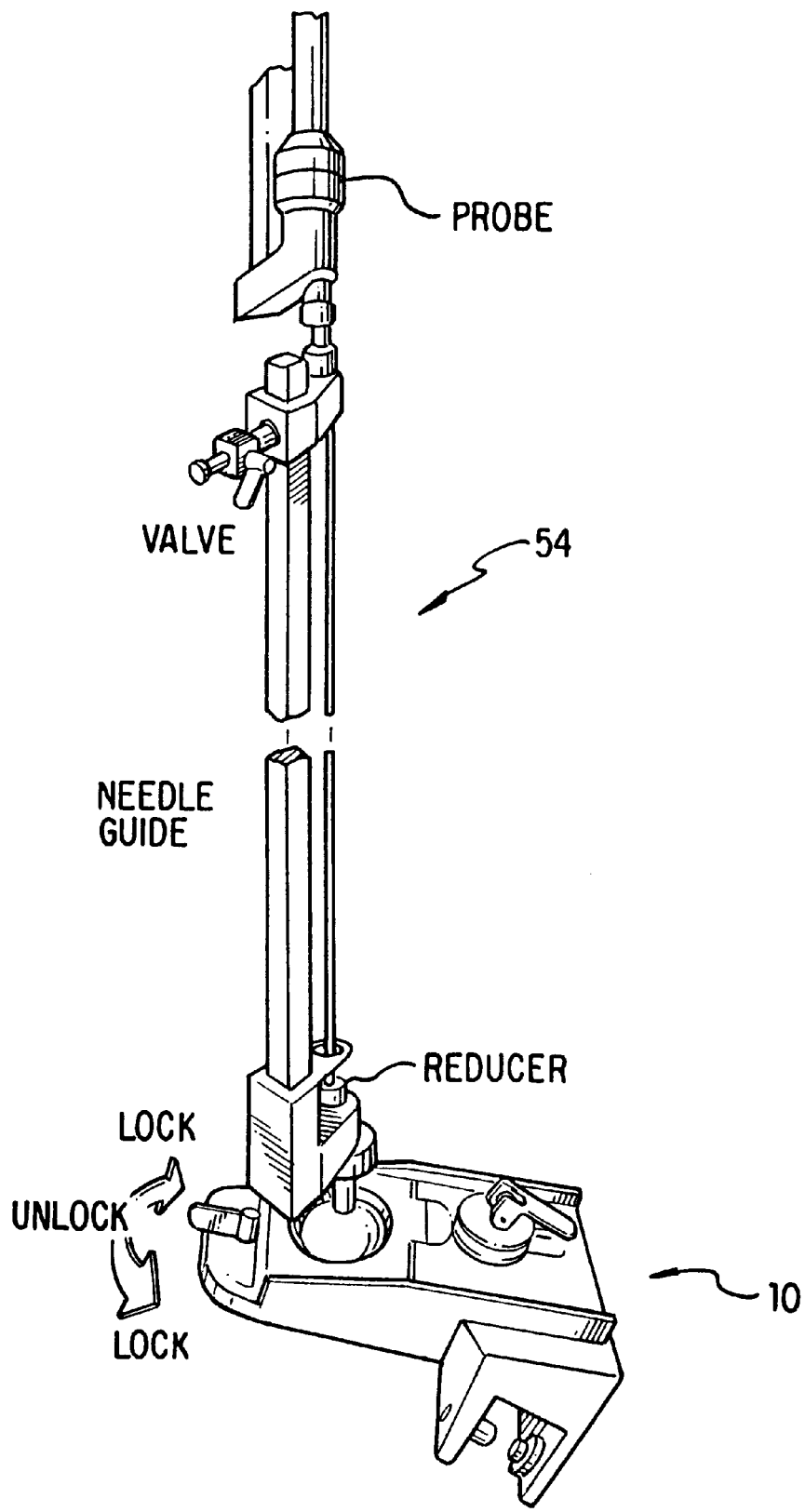
FIG. 12 illustrates an arrangement between a surgical platform and a needle guide according to an embodiment of the present invention.

FIG. 12 illustrates an arrangement of a surgical platform 10 relative to a surgical needle guide and probe arrangement 54 according to an embodiment of the present invention.

Figure 13:
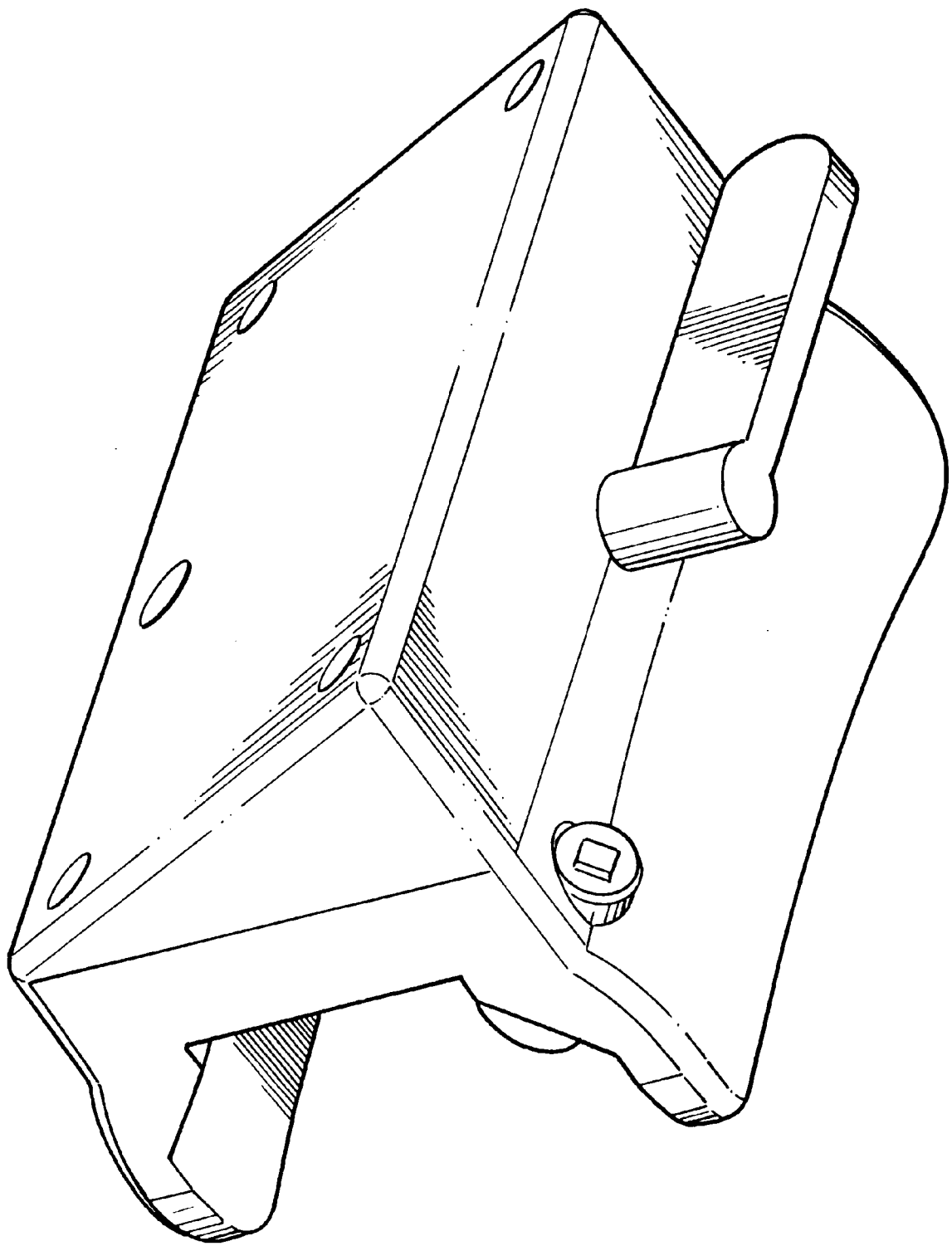
FIGS. 13 and 14 illustrate portions of a surgical platform according to an embodiment of the present invention.

FIG. 13 illustrates a portion of the surgical platform 10 which slides along the guiding arm 12 according to an embodiment of the present invention.

Figure 14:
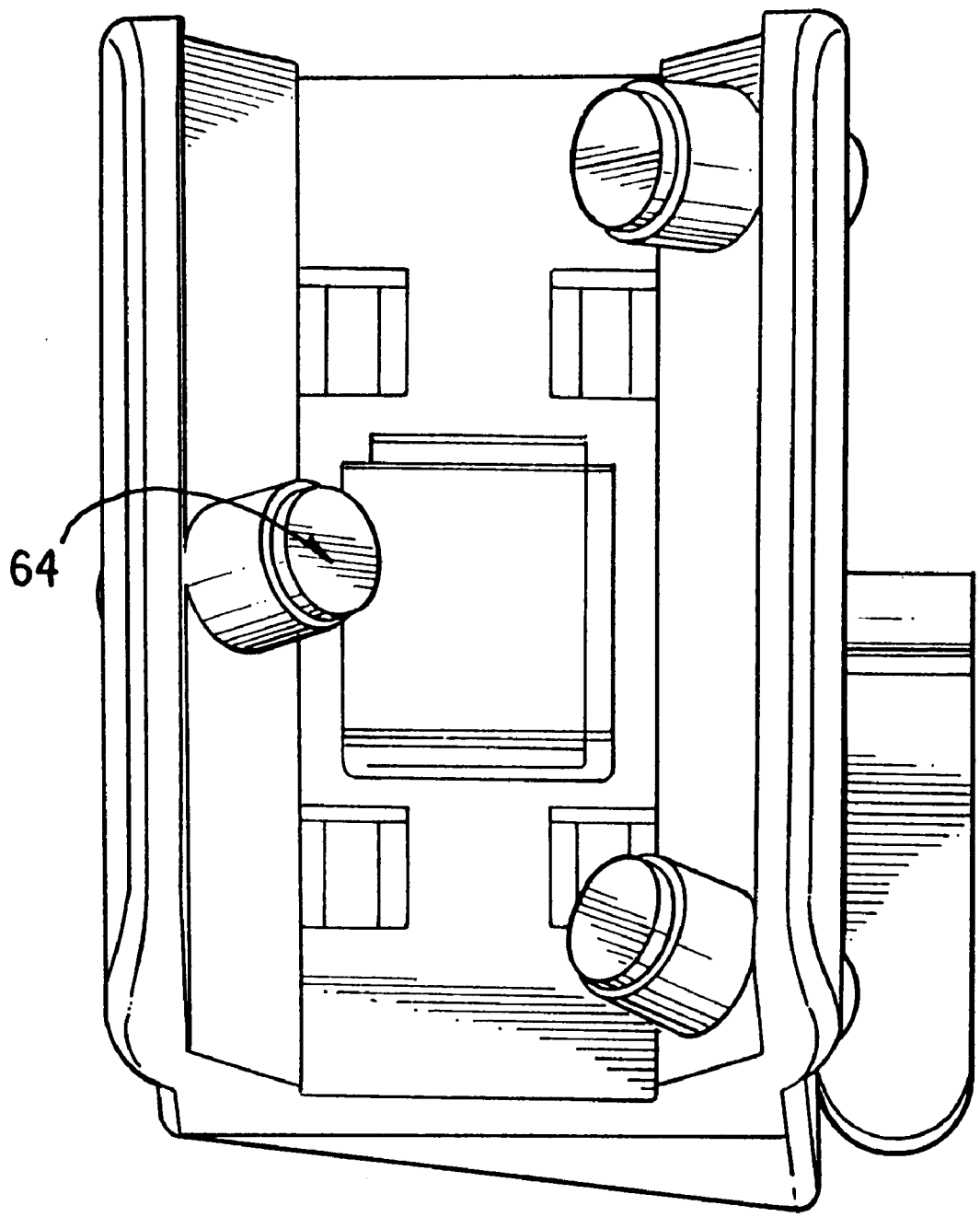

FIG. 14 illustrates an underside portion of the surgical platform which slides along the guiding arm via rollers 64.

Figure 15:
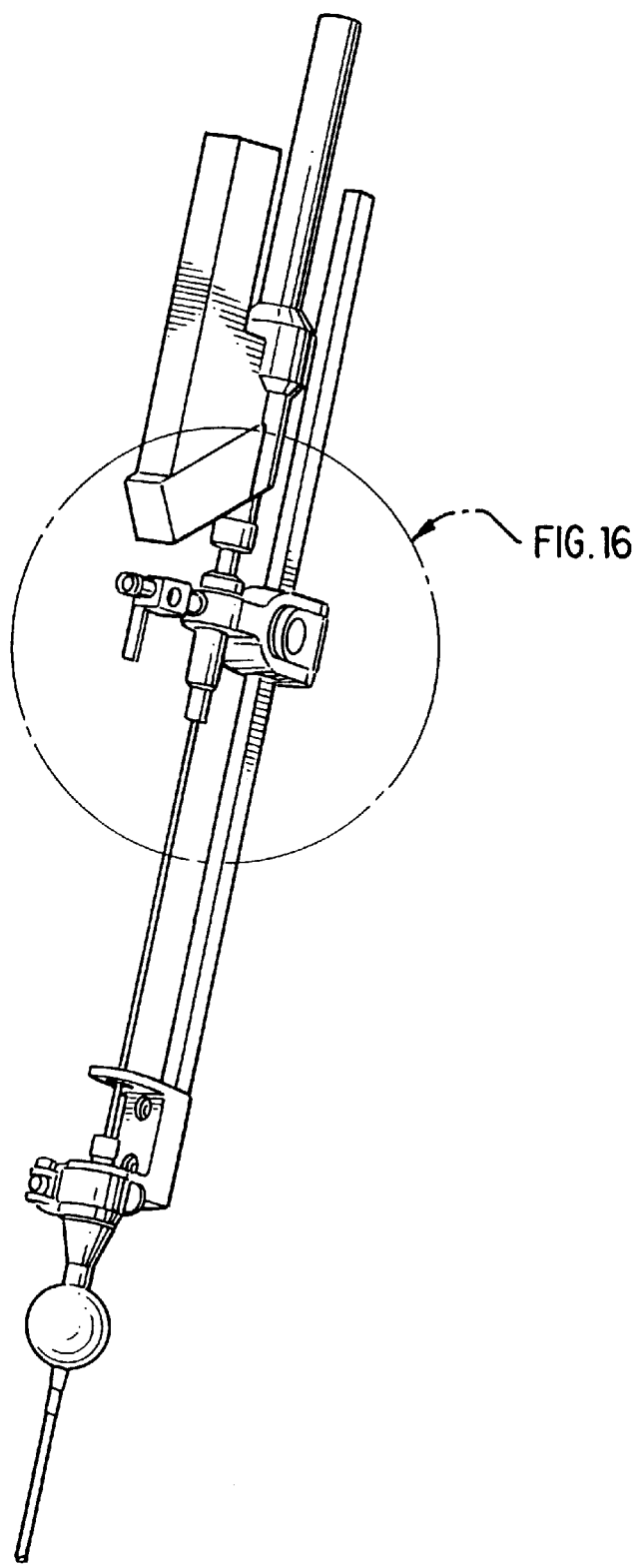
FIGS. 15, 16, 17 and 18 illustrate needle guide arrangements according to embodiments of the present invention.
Figure 16:
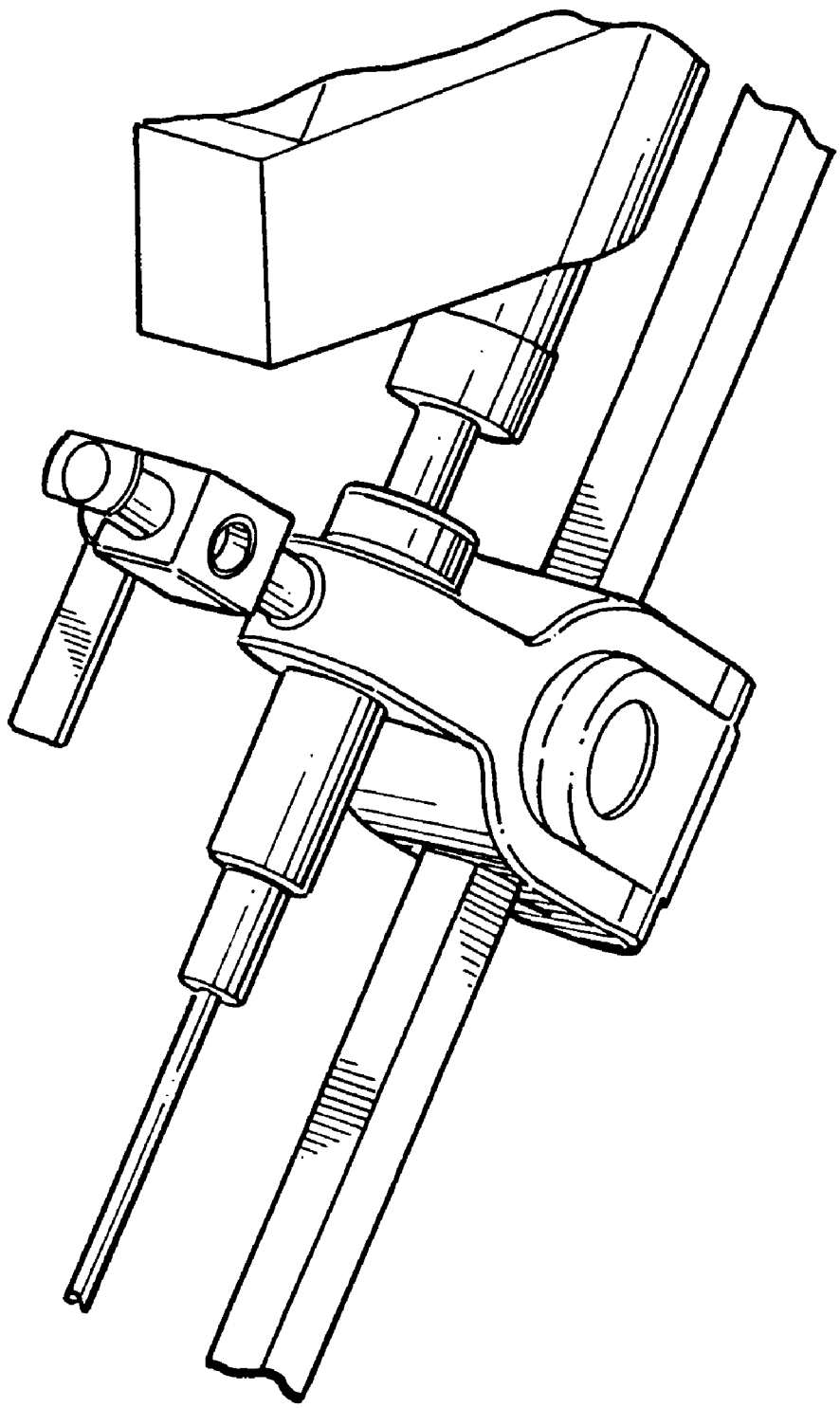

FIG. 15 illustrates a biopsy needle guide arrangement which may be implemented according to an embodiment of the present invention. Further detail of the surgical needle guide arrangement of FIG. 15 within the dotted line thereof is illustrated in FIG. 16.

Figures 17, 18:
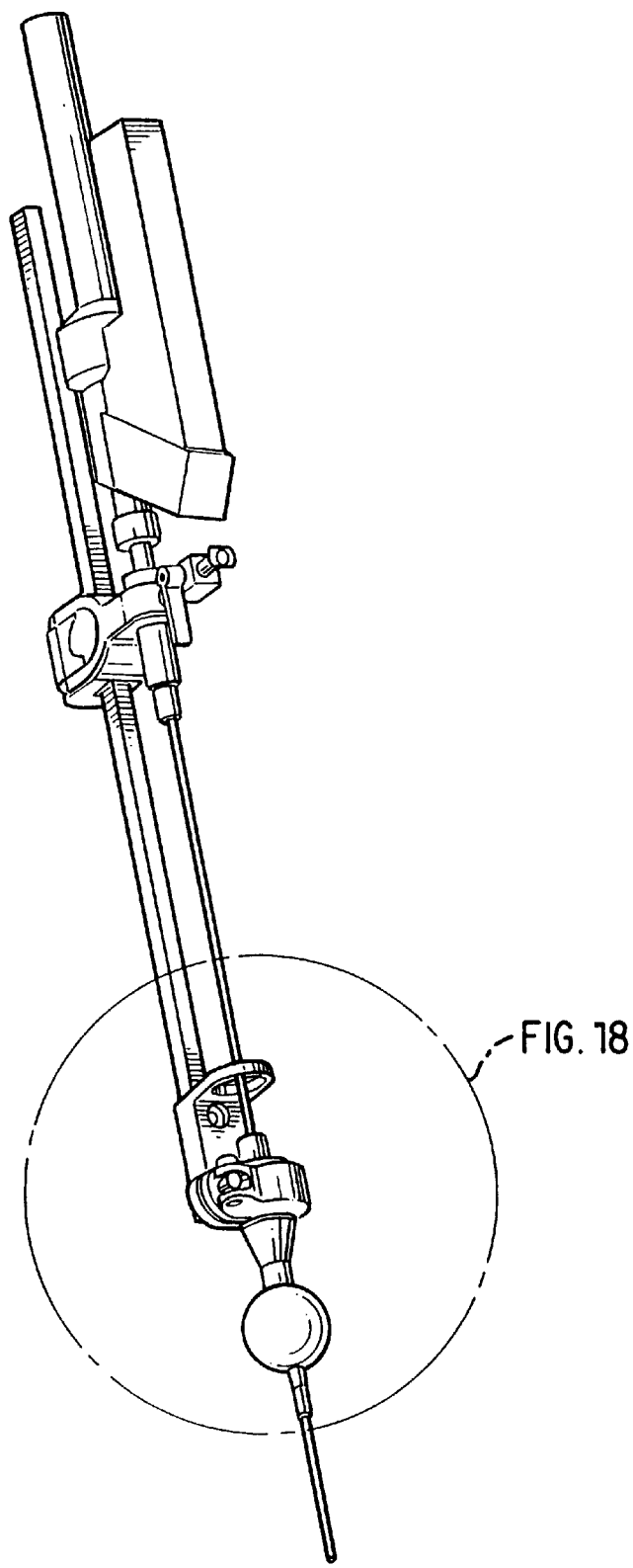
Figure 18:
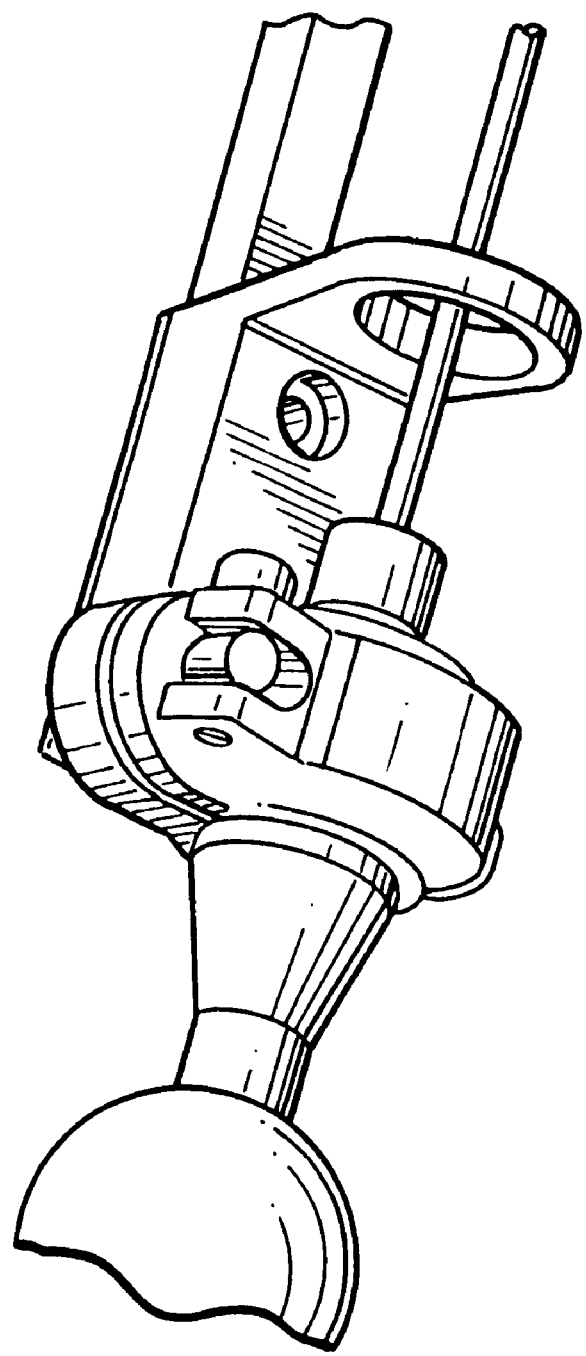

Similarly, FIG. 17 illustrates a needle guide which may be implemented according to an embodiment of the present invention. Further detail of the needle guide of FIG. 17 withing the dotted line thereof is illustrated in FIG. 18.

The ILD (intraoperative localization device) which tracks the location of the pivot point and the allignment of the surgical sleeve projecting therethrough is used to display an image based on the position of the pivot point and the position of the desired target, entry point and trajectory line. The localization software will project these points and lines on various image slices. As the surgeon moves the various surgical platforms, metal plate, ball joint and surgical sleeve, the alignment of the trajectory line relative to the ball joint position and surgical sleeve orientation are displayed on a screen. First, the localization software displays the pivot point relative to the trajectory line and provides an indication pointing out to the surgeon the distance between the closest point on the trajectory line, for example, relative to the pivot point. Once the pivot point is locked on to a position along the trajectory line, the navigational software then projects the relative position of the surgical sleeve axis relative to the trajectory line.

What is claimed is:

1. An image guided surgical system comprising:
   a guiding arm;
   a surgical platform slidable along said guiding arm;
   a metal plate connected to said surgical platform;
   a ball joint located in a center of said metal plate;
   a surgical sleeve passing through a middle of said ball joint;
   a localization device, said localization device included on said surgical sleeve;
   a computer, said computer storing an image-based coordinate system and said computer receiving position data from said localization device, said position data representative of a physical space position of said localization device; and
   a display device connected to said computer, said display device displaying said physical space position of said localization device in said image-based coordinate system.

2. The image guided surgical system of claim 1, wherein said surgical sleeve is a biopsy sleeve.

3. The image guided surgical system of claim 1 wherein said guiding arm is arc-shaped.

4. The image guided surgical system of claim 1 wherein said guiding arm is attached to an operating table when used with a patient.

5. The image guided surgical system of claim 1 further comprising a head clamp connected to said guiding arm, said head clamp connected to said guiding arm by a connection joint, said connection joint providing for rotational and translational movement of said guiding arm with respect to the head of a patient.

6. The image guided surgical system of claim 1 wherein said localization device includes infrared light emitting diodes.

7. The image guided surgical system of claim 1 wherein said localization device includes an electromagnetic emitting device.

8. The image guided surgical system of claim 1 wherein said localization device includes an ultrasonic emitting device.

9. The image guided surgical system of claim 1 wherein said image-based coordinate system is derived from a preoperative image volume of a patient.

10. The image guided surgical system of claim 9 wherein said preoperative image volume of the patient is a magnetic resonance image.

11. The image guided surgical system of claim 9 wherein said preoperative image volume of the patient is a CAT scan.

12. A method of performing a surgical procedure comprising the steps of:
   obtaining a preoperative image volume of a patient;
   selecting an entry point and a target point in said preoperative image volume to define a trajectory line;
   storing said preoperative image volume including said trajectory line in a computer to establish an image-based coordinate system;
   receiving physical space position data from a surgical guide at said computer;
   displaying said physical space position data of said surgical guide in said image-based coordinate system on a display device, said physical space position data of said surgical guide being displayed relative to said trajectory line;
   moving said surgical guide near said trajectory line by viewing said display of said space position data of said surgical guide relative to said trajectory line in said image-based coordinate system;
   aligning a pivot point of said surgical guide with a point along said trajectory line by viewing said display of said physical space position data of said surgical guide relative to said trajectory line in said image-based coordinate system; and
   pivoting said pivot point such that a surgical sleeve of said surgical guide is aligned along said trajectory.

13. The method of claim 12, wherein said surgical guide is a biopsy guide.

14. The method of performing a surgical procedure of claim 12 further comprising the step of calculating a distance between said target point and said pivot point of said surgical guide and displaying said distance on said display device.

15. The method of performing a surgical procedure of claim 12 further comprising the step of establishing a second trajectory line in said image-based coordinate system, said second trajectory line being parallel to said trajectory line.

16. The method of performing a surgical procedure of claim 12 wherein said physical space position data from said surgical guide is continuously received at said computer during the entire course of performing the surgical procedure.

17. The method of performing a surgical procedure of claim 12 wherein said physical space position data from said surgical guide is received at said computer as an infrared signal.

18. The method of performing a surgical procedure of claim 12 wherein said physical space position data from said surgical guide is received at said computer as an ultrasonic signal.

19. The method of performing a surgical procedure of claim 12 wherein said physical space position data from said surgical guide is received at said computer as an electromagnetic signal.

20. The method of performing a surgical procedure of claim 12 wherein said surgical guide is located external to the patient.

21. A surgical guide comprising:
- a head clamp, said head clamp including fasteners for securing said head clamp to an operating table;
- an arc-shaped guiding arm connected to said head clamp, said guiding arm connected to said head clamp at a first end to provide for rotational and translational motion of said guiding arm with respect to said head clamp;
- a locking knob connected to said guiding arm and a lever connected to said guiding arm, said locking knob engageable with said head clamp to prevent translational movement of said guiding arm with respect to said head clamp and said lever engageable with said head clamp to prevent rotational motion of said guiding arm with respect to said head clamp;
- a surgical platform slidable along said guiding arm, said surgical platform including a ball joint; and
- a surgical sleeve passing through said ball joint.

22. The surgical guide of claim 21 further comprising:
- a localization device, said localization device included on said surgical sleeve;
- a computer, said computer storing an image-based coordinate system and said computer receiving position data from said localization device, said position data representative of a physical space position of said localization device; and
- a display device connected to said computer, said display device displaying said physical space position of said localization device in said image-based coordinate system.

23. The surgical guide of claim 21 wherein said guiding arm can be simultaneously rotated and translated with respect to said head clamp.

24. The surgical guide of claim 21 wherein said surgical platform includes rollers, said rollers contacting said guiding arm to provide for motion of said surgical platform along said guiding arm.

25. The surgical guide of claim 21 wherein said guiding arm is attached to said head clamp at a second end to provide for rotational and translational motion of said guiding arm with respect to said head clamp.

* * * * *